United States Patent
Haven

(10) Patent No.: US 8,293,171 B2
(45) Date of Patent: Oct. 23, 2012

(54) BIO TURBO TECHNOLOGY OF REMOVING ETHYLENE GAS

(75) Inventor: Gerald Dean Haven, La Center, WA (US)

(73) Assignee: Gerald D. Haven, La Center, WA (US)

( * ) Notice: Subject to any disclaimer, the term of this patent is extended or adjusted under 35 U.S.C. 154(b) by 192 days.

(21) Appl. No.: 12/768,549

(22) Filed: Apr. 27, 2010

(65) Prior Publication Data

US 2011/0262302 A1   Oct. 27, 2011

(51) Int. Cl.
*A61L 9/00* (2006.01)
*A61L 2/00* (2006.01)
*A61L 2/04* (2006.01)
*A61L 2/18* (2006.01)
*A23L 11/00* (2006.01)
*C23F 11/00* (2006.01)
*F24F 3/16* (2006.01)

(52) U.S. Cl. ......... 422/4; 422/1; 422/5; 422/28; 422/29; 422/30; 62/78

(58) Field of Classification Search .............. 422/5, 28, 422/29, 30, 1, 4; 62/78, 331
See application file for complete search history.

(56) References Cited

U.S. PATENT DOCUMENTS

| | | | | |
|---|---|---|---|---|
| 788,557 | A | * | 5/1905 | Sahlstrom ............... 422/186.18 |
| 935,457 | A | * | 9/1909 | Bridge ...................... 422/186.18 |
| 5,430,228 | A | * | 7/1995 | Ciambrone et al. .......... 588/320 |
| 6,358,374 | B1 | * | 3/2002 | Obee et al. .................. 204/157.3 |
| 7,407,624 | B2 | * | 8/2008 | Cumberland et al. .......... 422/28 |
| 2004/0120845 | A1 | * | 6/2004 | Potember et al. .................. 422/4 |
| 2005/0089458 | A1 | * | 4/2005 | Oke ............................. 422/207 |
| 2010/0158749 | A1 | * | 6/2010 | Benedek et al. .................. 422/4 |
| 2010/0296966 | A1 | * | 11/2010 | Bae et al. .......................... 422/4 |

FOREIGN PATENT DOCUMENTS

| | | | | |
|---|---|---|---|---|
| JP | 58183928 | A | * | 10/1983 |
| JP | 01300184 | A | * | 12/1989 |
| JP | 2001162116 | A | * | 6/2001 |

OTHER PUBLICATIONS

JP 58-183928, English Abstract, 1983.*
JP 2001-162116, English translation, 2001.*

* cited by examiner

*Primary Examiner* — Regina M. Yoo

(57) ABSTRACT

The present invention provides with a method of purifying air with significant content of ethylene gas. Bacteria, pathogens, molds, fungus and ethylene gas are removed by using ozone and air filtration technology. This process is useful for storages and production facilities where ethylene might be harmful for perishable products.

5 Claims, 1 Drawing Sheet

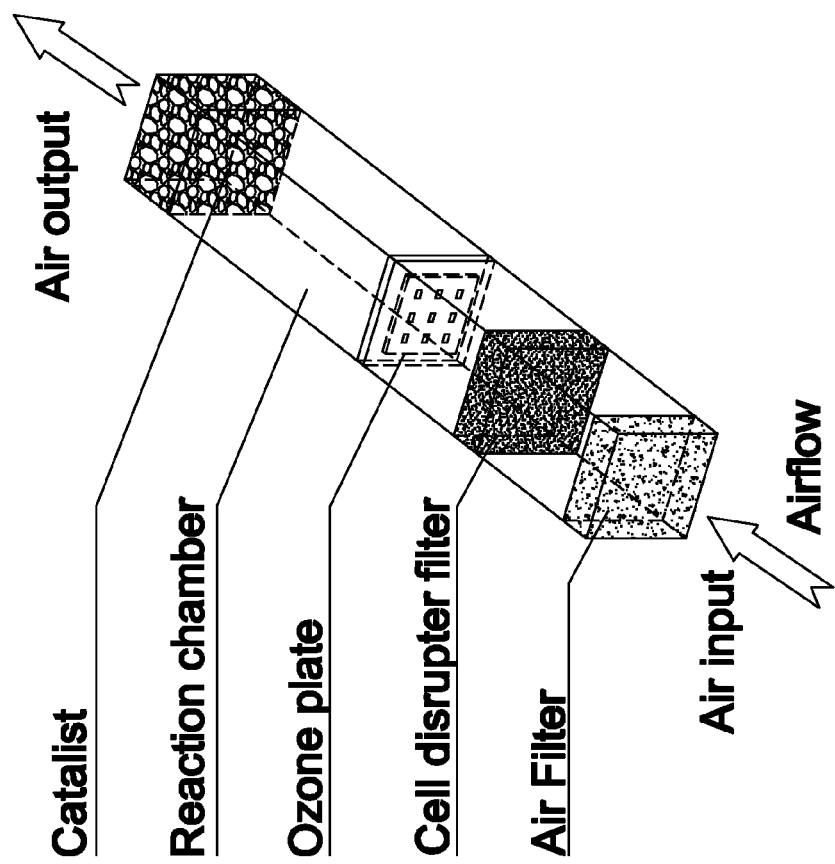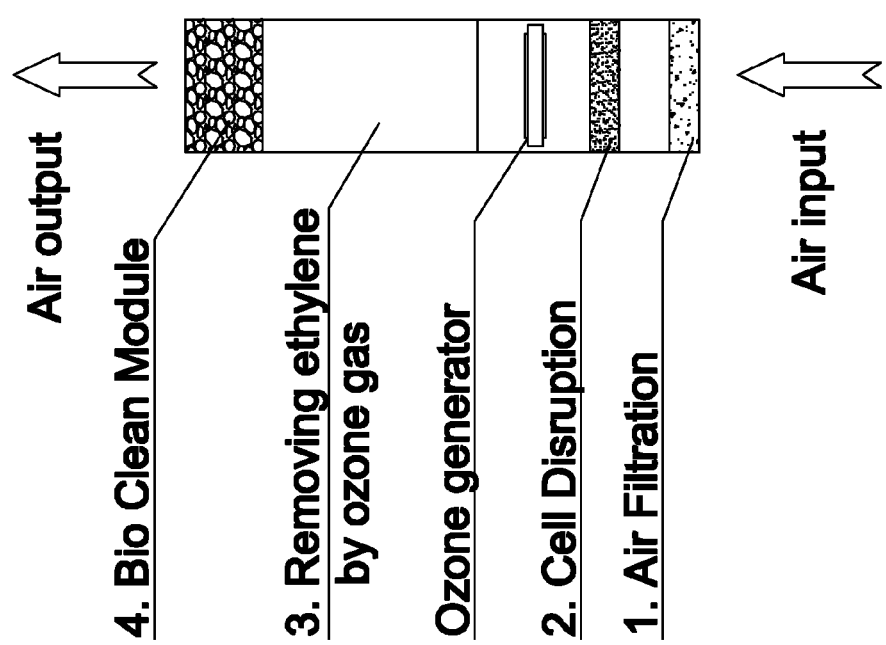

BIO TURBO TECHNOLOGY OF REMOVING ETHYLENE GAS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM, LISTING COMPACT DISC APPENDIX

Not Applicable

BACKGROUND OF THE INVENTION

This invention relates generally for using of filtration devices to eliminate ethylene gas and contaminates like bacteria, pathogens, molds, fungus from the storage environment which would adversely affect the perishable products.

Ethylene gas ($C_2H_4$) is an odorless, colorless gas that exists in nature and is also created by man-made sources. Not easily detectable, it exists where produce is stored. In nature, the largest producers are plants and plant products (fruits, vegetables and floral products) which produce ethylene within their tissues and release it into the surrounding atmosphere. It is a very small, simple molecule that exists as a gas at biological temperatures. Plants use ethylene as a hormone. It is also a by-product of man-made processes, such as combustion. Ethylene, also known as the 'death' or 'ripening hormone', plays a regulatory role in many processes of plant growth, development and eventually death. Fruits, vegetables, and flowers contain receptors which serve as bonding sites to absorb free atmospheric ethylene molecules. The common practice of placing a tomato, avocado or banana in a paper bag to hasten ripening is an example of the action of ethylene on produce. Increased levels of ethylene contained within the bag, released by the produce itself, serve as a stimulant after reabsorption to initiate the production of more ethylene. Even small amounts of ethylene gas during shipping and storage causes most fresh produce to deteriorate faster. The overall effect is to hasten ripening, aging, and eventually spoilage. Removing ethylene from the storage extends the life of produce.

Molds are tiny microscopic organisms that digest organic matter and reproduce by releasing spores. The spores in turn need moisture to grow, reproduce and continue the cycle. Molds grow best in conditions of excess moisture, caused by either high humidity or water seeping into the storage area. Molds that develop within wineries may result in damage to walls and barrels, as well as producing unacceptable odors.

The invention relates more particularly to the elimination of ethylene gas specifically from storage environment so that the immediate area surrounding the products in an enclosed area would be free of harmful ethylene concentration as well as bacteria, pathogens and mold spores.

BRIEF SUMMARY OF THE INVENTION

The main idea of the invention is to minimize the amount of ethylene gas and produce clean, healthy air in cold rooms, wineries and storage areas used for produce storing. The Bio Turbo ethylene removing technology uses four stages of air cleaning and ethylene eliminating.

At the beginning, cold room's (storage) air is pulled to Bio Turbo system for cleaning: the filters (air filter and demister filter) remove visible particles, bacteria, pathogens, molds and fungus. Then the primary purified air is pulled to reaction chamber. Ozone gas ($O_3$) generated in special ozone chamber also goes to the reaction chamber. The reaction between ethylene gas and ozone breaks the molecule of ethylene. The next stage is to break the ozone molecule $O_3$ which could remain. The Bio Turbo technology converts ozone molecule $O_3$ into oxygen $O_2$ by using catalyst.

Finally, pure air free of ethylene and contaminants is pulled back into the storage. This circulation process continues constantly.

BRIEF DESCRIPTION OF THE SEVERAL VIEWS OF THE DRAWING

The FIG. 1 is the drawing shows the schematic explanation of Bio-Turbo technology of removing ethylene gas for more understanding of present invention.

There are shown the four-stage method of air cleaning and ethylene removing on the drawing. Ambient air from the storage goes one by one through the following steps:
  Air Filtration;
  Cell Disruption;
  Removing ethylene by ozone gas;
  Bio Clean Module (removing ozone gas by catalyst)
Purified air goes back to the storage. This is a circulation process which continues constantly.

DETAILED DESCRIPTION OF THE INVENTION

The Bio Turbo technology is a four stage process that purifies air and removes ethylene gas, airborne pathogens and bacteria from cold rooms (storages). This technology includes: air filtration by air filter, cell disruption by anti-microbial cell disrupter, elimination of ethylene gas by reaction between ozone and ethylene and converting ozone into oxygen by using catalyst. The four stages described below goes one by one and it shows full Bio Turbo technology process.

Stage 1: Air Filtration

At the beginning of Bio Turbo Technology a particulate air filter is used in order to prepare air to the next stages of its cleaning. Air filter pad which is situated at the intake removes solid particulates such as dust, pollen, mold, and bacteria from the air. Filter pad is a device composed of fibrous materials. Ambient air from storage environment is pulling by fan located inside a unit through air filter. All visual and significant particles are removed from air during this process.

Stage 2: Cell Disruption

After primary purification by air filter, air goes to cell disrupter filter. An anti-microbial chemical is applied to the surface of a specially designed disrupter. This anti-microbial chemical works by piercing and rupturing the cell membrane of the cells that makes up these airborne pathogens as they pass by. The cell disruption process stops the normal life development and destroys the cell with high efficiency. This stage can be especially active on mold spores. After this stage purified air with ethylene gas goes to reaction chamber.

Stage 3: Removing Ethylene by Ozone Gas

At this stage the positive effects of ozone is used to eliminate ethylene gas. Ozone is proven to be very effective with 99.99% efficiency rate. The ozone is generated in by high voltage applied to a perforated stainless steel plate attached to each side of a glass plate. This voltage is an alternating current in the 6K volt range. The voltage is generated by 115 Volts applied to the primary windings of a step up transformer. The secondary windings of the transformer produce 6000 volts to each plate causing the air to ionize producing the ozone. The ozone is then drawn into the reaction chamber which consists of a large aluminum box. The reaction between ethylene and ozone has place in this box. The aluminum chamber has a partition down the center, attached at the ozone generator end and extends to the far end of the chamber. The partition does not attach at the far end but has a 1.0" gap for air flow. This causes the air to flow down one half of the chamber and cross over to the other side of the chamber and return down the other side. This allows for more contact time between the ethylene and the ozone to eliminate the maximum amount of ethylene after their reaction.

Stage 4: Bio Clean Module

Some amount of ozone gas may persist after ozone-ethylene reaction. Ozone ($O_3$) is a tri-atomic molecule consisting of three oxygen atoms. It is an allotrope of oxygen that is much less stable than $O_2$. A high concentration of ozone is considered a pollutant at ground level and may have harmful effects on the respiratory systems of animals and humans. The purpose of this final stage is removing any ozone might be present in air after ethylene-ozone reaction. A catalyst is used in order to get rid any remaining ozone. The catalyst creates a reaction breaking down the ozone molecule. Because of the catalyst, ozone has now broken down to oxygen. From here the clean oxygen is released back into the environment. In this way, ozone is prevented from leaving the system. The air is then released back into the storage area without ozone. Granulated manganese is used as catalyst. The amount of catalyst is determined by the amount of ozone generated and the size of the reaction chamber.

I claim:

1. A method of eliminating solid particulates, airborne pathogens, and ethylene gas from air in a storage environment, the method comprising the steps of:

a) filtering the air present in the storage environment through an air filter to provide primary purified air, wherein the air filter comprises fibrous materials, wherein the air present in the storage environment is pulled through the air filter by a fan, and wherein the air filter removes the solid particulates;

b) filtering the primary purified air through a demister filter to provide secondary purified air and the ethylene gas, wherein the demister filter comprises a cell disruption filter having an anti-microbial chemical applied to its surface for piercing and rupturing the airborne pathogens' cell membrane, and wherein the demister filter removes the airborne pathogens;

c) reacting the secondary purified air and the ethylene gas with ozone in a reaction chamber to provide tertiary purified air and ozone, wherein the ozone is generated by high voltage applied to a perforated stainless steel plate attached to each side of a glass plate, and wherein the ozone removes the ethylene gas;

d) reacting the ozone in the tertiary purified air with granulated manganese outside the reaction chamber to provide oxygen and clean air, wherein the tertiary purified air and ozone is passed through the granulated manganese; and e) returning the oxygen and clean air to the storage environment.

2. The method of claim 1, wherein the solid particulates comprise dust, pollen, molds, and bacteria.

3. The method of claim 1, wherein the airborne pathogens comprise bacteria, molds, and fungus.

4. The method of claim 1, wherein the storage environment comprise fruits, vegetables and floral products.

5. The method of claim 1, wherein the storage environment comprise cold rooms, wineries and storage areas used for storing produce.

* * * * *